United States Patent
Serrurier et al.

(10) Patent No.: US 10,060,099 B2
(45) Date of Patent: Aug. 28, 2018

(54) WEAR INDICATOR FOR A WEAR MEMBER OF A TOOL

(71) Applicant: Caterpillar Inc., Peoria, IL (US)

(72) Inventors: Doug Serrurier, Morton, IL (US); Arun Venugopal, Chennai (IN)

(73) Assignee: Caterpillar, Inc., Deerfield, IL (US)

( * ) Notice: Subject to any disclaimer, the term of this patent is extended or adjusted under 35 U.S.C. 154(b) by 141 days.

(21) Appl. No.: 15/178,657

(22) Filed: Jun. 10, 2016

(65) Prior Publication Data

US 2017/0356165 A1 Dec. 14, 2017

(51) Int. Cl.
| | |
|---|---|
| *E02F 9/26* | (2006.01) |
| *E02F 9/28* | (2006.01) |
| *G01N 3/56* | (2006.01) |
| *G06F 17/50* | (2006.01) |
| *E21B 12/02* | (2006.01) |
| *B33Y 10/00* | (2015.01) |
| *B33Y 80/00* | (2015.01) |
| *E02F 3/40* | (2006.01) |

(52) U.S. Cl.
CPC ............ *E02F 9/267* (2013.01); *E02F 9/2883* (2013.01); *E21B 12/02* (2013.01); *G01N 3/56* (2013.01); *G06F 17/50* (2013.01); *B33Y 10/00* (2014.12); *B33Y 80/00* (2014.12); *E02F 3/40* (2013.01); *G06F 2217/12* (2013.01)

(58) Field of Classification Search
CPC . E02F 9/267; E02F 9/2883; E02F 3/40; E02F 9/28; G01N 3/56; G06F 17/50; G06F 2217/12; B33Y 80/00

USPC .......... 116/200, 208, 209, 212; 138/36, 104, 138/110, 137; 305/43, 46, 185

See application file for complete search history.

(56) References Cited

U.S. PATENT DOCUMENTS

| | | | | |
|---|---|---|---|---|
| 2,102,784 A | * | 12/1937 | Bridges | B60C 11/24 116/201 |
| 2,468,905 A | | 5/1949 | Warren, Jr. | |
| 3,578,055 A | * | 5/1971 | French | B60C 11/24 116/208 |
| 3,729,041 A | * | 4/1973 | Kubota | B05D 5/061 152/523 |
| 3,929,179 A | | 12/1975 | Hines | |
| 4,995,176 A | * | 2/1991 | Briscoe | E02F 3/8152 172/751 |

(Continued)

FOREIGN PATENT DOCUMENTS

| | | |
|---|---|---|
| CA | 2445795 | 1/2004 |
| WO | WO 2006/032107 | 3/2006 |

(Continued)

*Primary Examiner* — R. A. Smith
*Assistant Examiner* — Tania Courson
(74) *Attorney, Agent, or Firm* — Finnegan, Henderson, Farabow, Garrett & Dunner, LLP

(57) ABSTRACT

A wear indicator is provided for a wear member of a machine wherein the wear member is subject to wear during use of the machine. The wear indicator may include a plug member configured to be positioned in a region of the wear member subject to wear. The plug member may be oriented with a central axis extending in a direction substantially parallel to a direction of wear of the wear member. The wear indicator may include a plurality of perceptibly different and distinct axial cross sections taken perpendicular to the central axis of the plug member in axially spaced planes along the central axis.

25 Claims, 8 Drawing Sheets

(56) References Cited

U.S. PATENT DOCUMENTS

| | | | |
|---|---|---|---|
| 5,144,762 A | 9/1992 | Robinson | |
| 5,241,765 A * | 9/1993 | Jones | E02F 3/60 172/772 |
| 5,511,636 A * | 4/1996 | Tanaka | F16D 65/08 188/1.11 W |
| 5,796,349 A * | 8/1998 | Klein | F16C 17/04 116/208 |
| 5,913,605 A * | 6/1999 | Jusselin | E02F 9/28 172/772 |
| 5,937,549 A * | 8/1999 | Bender | E02F 9/2825 172/772 |
| 5,983,949 A * | 11/1999 | Pohle | F16L 11/124 138/104 |
| 6,494,548 B2 * | 12/2002 | Courtemanche | B62D 55/244 305/167 |
| 7,011,126 B2 * | 3/2006 | Heinen | B60C 11/032 152/154.2 |
| 7,144,183 B2 * | 12/2006 | Lian | E02F 9/2841 172/772 |
| 7,424,936 B2 * | 9/2008 | McClellan | F16D 66/028 188/1.11 R |
| 7,536,811 B2 * | 5/2009 | McClanahan | E02F 9/2833 172/772.5 |
| 7,698,839 B1 | 4/2010 | Phillips et al. | |
| D751,610 S * | 3/2016 | Serrurier | D15/28 |
| 9,476,689 B2 * | 10/2016 | Steed | G01B 7/02 |
| 9,724,697 B2 * | 8/2017 | Steed | B02C 4/00 |
| 9,732,495 B2 * | 8/2017 | Congdon | E02F 3/8152 |
| 9,758,947 B2 * | 9/2017 | Serrurier | E02F 9/2883 |
| 2003/0138655 A1 * | 7/2003 | Watanabe | B60S 1/38 428/523 |
| 2009/0114322 A1 | 5/2009 | O'Brien | |
| 2012/0160150 A1 * | 6/2012 | Handfield | B62M 27/02 116/208 |
| 2014/0102791 A1 * | 4/2014 | Dupont | E21B 12/02 175/39 |
| 2014/0173948 A1 | 6/2014 | Ok et al. | |
| 2014/0173949 A1 * | 6/2014 | Karlsson | E02F 9/2825 37/455 |
| 2015/0266527 A1 | 9/2015 | Akinlua et al. | |

FOREIGN PATENT DOCUMENTS

| | | |
|---|---|---|
| WO | 2007128058 | 11/2007 |
| WO | 2012163431 | 12/2012 |
| WO | WO 2015/126923 | 8/2015 |
| WO | 2017083691 | 5/2017 |

* cited by examiner

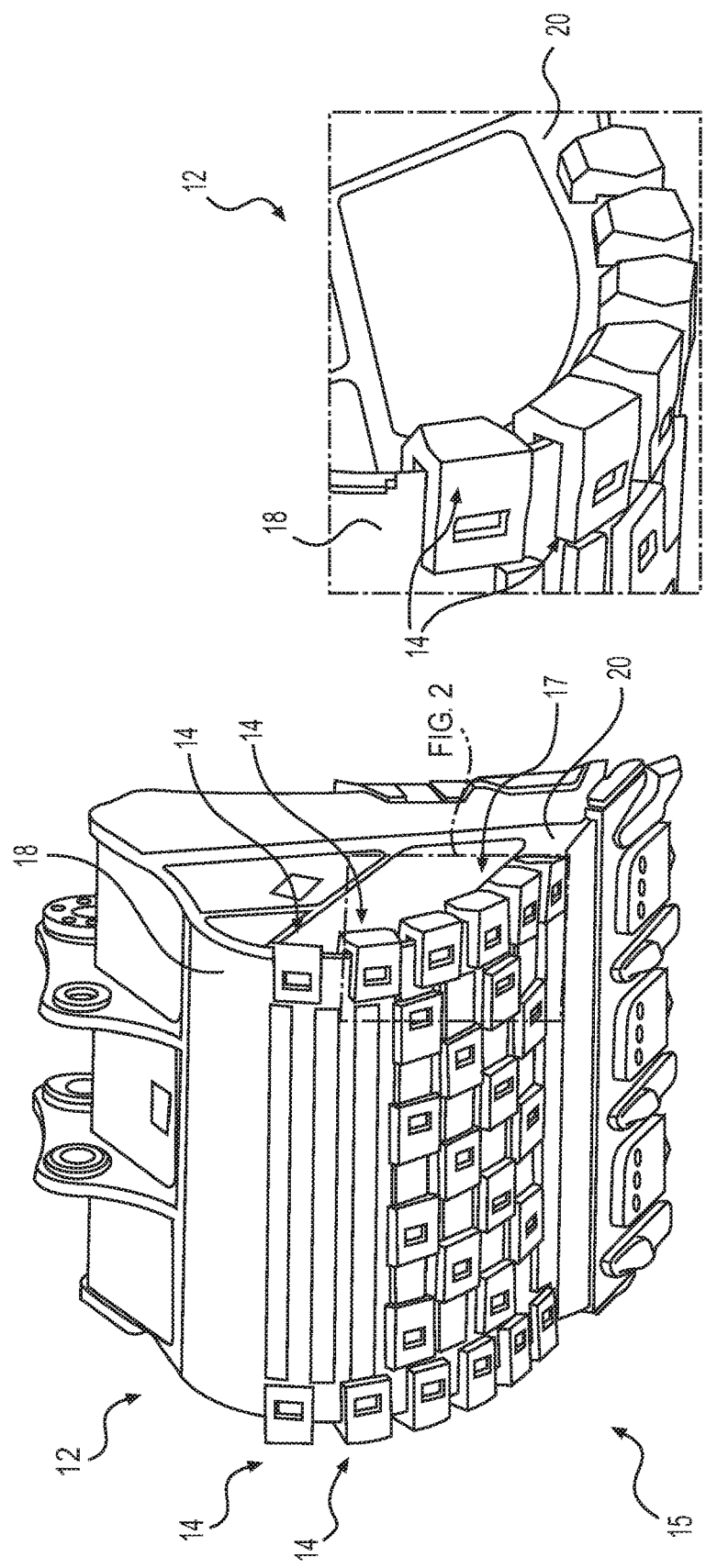

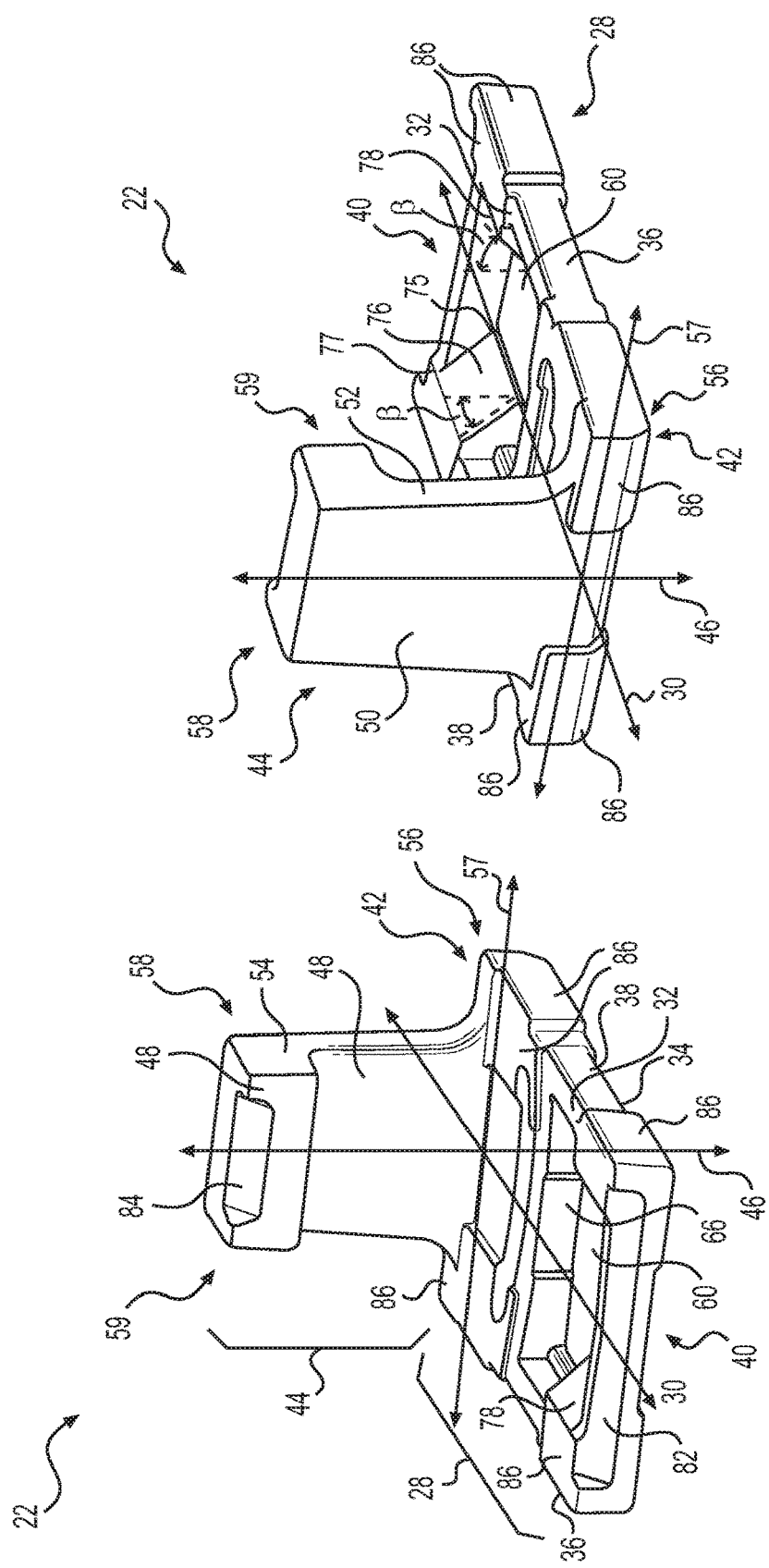

WEAR INDICATOR FOR A WEAR MEMBER OF A TOOL

TECHNICAL FIELD

The present disclosure relates generally to a wear indicator, and more particularly, to a wear indicator for a wear member of a tool.

BACKGROUND

Many earth-working machines, such as, for example, loaders, excavators, hydraulic mining shovels, cable shovels, bucket wheels, and draglines, include tools for moving material (e.g., for digging material out of the earth). These tools are often subjected to extreme wear from abrasion and impacts experienced while moving the material. In order to mitigate the wear, replaceable wear members are fit to the tools and engage the material being moved.

U.S. Patent Application Publication No. 2015/0266527 A1 (the '527 publication) to Akinlua et al. describes a link for a track assembly of a machine. The link body includes a first surface configured to contact a rotatable element of the track assembly and a second surface configured to contact a track shoe coupled to the link body. The link includes a plurality of markings defined on the link body proximal to the first surface, wherein each of the markings is indicative of progressive wear of the link body with respect to the first surface.

The system of the '527 publication may provide certain benefits in monitoring progressive wear of a wear element of a machine. However, further improvements that would facilitate identification of the extent of wear on a surface of a wear element of a machine, and in particular that would enable automated identification of the extent of wear may be desirable. The disclosed embodiments may help solve this and other problems.

SUMMARY

One aspect of this disclosure is directed to a wear indicator for a machine wear member subject to wear during use of the machine. The wear indicator may comprise a plug member configured to be positioned in a region of the machine wear member subject to wear. The plug member may be oriented with a central axis extending in a direction substantially parallel to a direction of wear of the machine wear member. The wear indicator may include a plurality of perceptibly different and distinct axial cross sections taken perpendicular to the central axis of the plug member in axially spaced planes along the central axis.

Another aspect of this disclosure is directed to a wear member of a machine. The wear member may include at least one surface subject to wear during operation of the machine. The at least one surface may include at least one wear indicator configured to provide an indication of an amount of wear of a region of the at least one surface of the wear member. The at least one wear indicator may comprise a plug configured to be positioned in the region of the at least one surface of the wear member. The plug may be oriented with a central axis extending in a direction substantially parallel to a direction of wear of the machine wear member. The wear indicator may include a plurality of perceptibly different and distinct axial cross sections taken perpendicular to the central axis of the plug in axially spaced planes along the central axis.

Yet another aspect of this disclosure is related to a wear indicator detection system for automatically detecting an amount of wear on a surface of a wear member of a machine. The wear indicator detection system may include one or more sensory devices positioned within a range of detection of at least one wear indicator located in a surface region of the wear member of the machine. Each of the one or more sensory devices may be configured to discern perceptibly different and distinct regions of the at least one wear indicator as the surface of the wear member is worn away by different amounts to expose a plurality of spaced regions of the wear indicator.

BRIEF DESCRIPTION OF THE DRAWINGS

FIG. 1 is a perspective view of a plurality of exemplary disclosed wear member systems installed on a tool;

FIG. 2 is an enlarged perspective view of several of the wear member systems of FIG. 1;

FIG. 4 is a perspective view of an exemplary disclosed mounting base of the wear member system of FIG. 3;

FIG. 5 is another perspective view of the mounting base of FIG. 4, from a different angle;

DETAILED DESCRIPTION

FIGS. 1 and 2 illustrate exemplary wear member systems 14, which may be attached to a tool 12. For example, tool 12 may be a bucket (as shown in FIG. 1), a blade, a shovel, a crusher, a grapple, or a ripper, and may be associated with an earth-working machine (e.g., a loader, an excavator, a hydraulic mining shovel, a cable shovel, a bucket wheel, a dragline, or another type of earth-working machine). Tool 12 may be used for moving material (e.g., for digging material out of the earth). Wear member systems 14 may be attached to heels 15, 17 of tool 12, and may mitigate wear from abrasion and impacts experienced by heels 15, 17 while moving the material.

Figure 3:
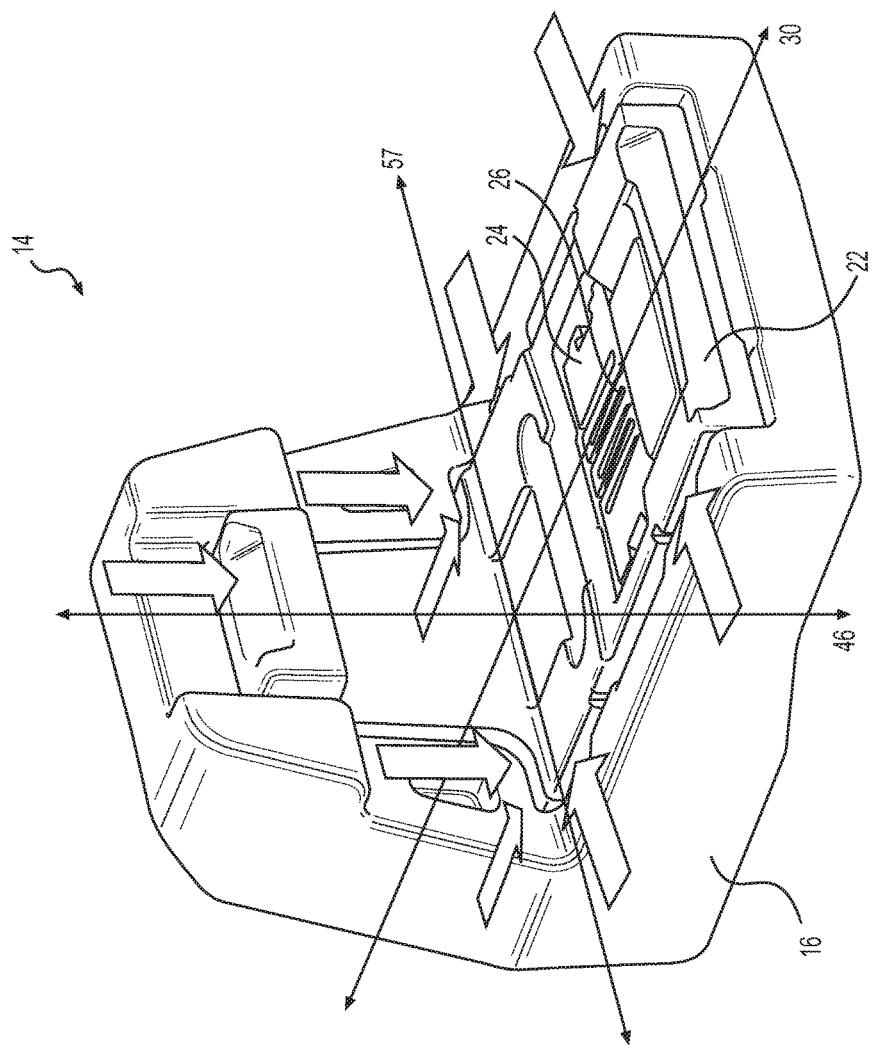
FIG. 3 is a perspective view of one of the wear member systems of FIGS. 1 and 2.

Referring to FIG. 3, each wear member system 14 may include a mounting base 22, a wear member 16, a retainer 24, and a plug 26. Mounting base 22 may be configured to be attached (e.g., fixedly) to a first surface 18 and a second surface 20 of tool 12 (referring to FIGS. 1 and 2). Wear member 16 may be configured to be removably coupled to tool 12 via mounting base 22. Retainer 24 may be configured to keep wear member 16 coupled to mounting base 22 when in a mounted position, and plug 26 may be configured to protect retainer 24. One or more wear indicators 118 (shown in FIG. 6) may be incorporated into one or more surfaces of wear member 16 in order to provide a perceptible indication of the amount of wear at those surfaces of wear member 16. A "perceptible" indication of the amount of wear refers to a difference in one or more characteristics of portions of the wear indicator that become exposed as a result of wear at a surface of the wear member and that may be detected by either a human observer or by some type of automated sensory device. Some examples of characteristics of the wear indicator associated with a worn area of a surface that may be detected by one or both of a human observer and an automated sensory device may include portions of the wear indicator that have at least one of different shape, different color, different material, different texture, different reactivity to electromagnetic radiation, different reflectivity of electromagnetic radiation, and different absorptivity of electromagnetic radiation. As described in more detail below, wear indicator(s) 118 may also enable automatic identification of the amount of wear sustained by each of a plurality of regions on various wear surfaces of wear member 16. Although the figures illustrate a wear member system configured for attaching a wear member to a tool such as a bucket, one of ordinary skill in the art will recognize that wear indicators in accordance with various implementations of this disclosure may be incorporated into wear surfaces of any wear member of a machine, wherein the wear member and wear indicator(s) are subject to wear during use of the machine.

FIGS. 4 and 5 illustrate an exemplary mounting base 22 from a variety of angles. As shown, mounting base 22 may include a generally planar first base portion 28 that extends in a longitudinal direction 30. Mounting base 22 may also include a generally planar second base portion 44, which may extend from first base portion 28 in a direction generally perpendicular to first base portion 28, shown as vertical direction 46.

First base portion 28 may be generally rectangular, and may have an inward surface 32 configured to be attached to tool 12. First base portion 28 may also have an outward surface 34 opposite inward surface 32. In addition, first base portion 28 may have a pair of opposite sides 36, 38 that extend generally parallel to longitudinal direction 30. First base portion 28 may also have a pair of opposite ends, first end 40 and second end 42, which extend in a direction generally perpendicular to longitudinal direction 30, shown as latitudinal direction 57.

Referring to FIGS. 4 and 5, first base portion 28 may define a first opening 60, which may be configured to receive a portion of wear member 16 and a retainer 24 (referring to FIG. 3). First opening 60 may extend along vertical direction 46 from outward surface 34, through first base portion 28, to inward surface 32. First opening 60 may be fully enclosed by first base portion 28. First opening 60 may include a first portion configured for receiving a portion of wear member 16, and a second portion contiguous with the first portion for receiving retainer 24. The first and second portions of first opening 60 may have different shapes, e.g., polygon, square, circle, oval, trapezoid, or other shapes.

First opening 60 may have a surface 66, and a pair of opposite ends that run parallel to longitudinal direction 30. Opposite ends of first opening 60 may include a pair of opposing flanges, which may extend inward toward one another from lower regions of the opposite ends of first opening 60, adjacent outward surface 34. The opposing flanges may be configured to facilitate retention of retainer 24 when retainer 24 is installed in first opening 60.

Portions of first opening 60 may be defined by opposing angled surfaces 76, 78 that converge toward each other as they extend from inward surface 32 to outward surface 34. As a result of the convergence, at least a portion of a perimeter 77 of first opening 60, which is defined by angled surfaces 76, 78, at inward surface 32 may be larger than another portion of a perimeter 75 of first opening 60, which is defined by surfaces 76, 78, at outward surface 34. As shown in FIGS. 4-5, angled surfaces 76, 78 may be symmetrical about vertical direction 46. For example, both angled surfaces 76, 78 may extend at an angle β of about 45 degrees relative to vertical direction 46. Alternatively, both angled surfaces 76, 78 may extend at another angle relative to vertical direction 46. Alternatively, surfaces 76, 78 may be asymmetrical about vertical direction 46, and may extend at different angles relative to vertical direction 46.

First base portion 28 may also include a plurality of loading pads 86 configured to contact tool 12 and wear member 16. Loading pads 86 may be configured to transfer loads from wear member 16 to mounting base 22 and tool 12 in directions generally perpendicular to planar first base portion 28, generally perpendicular to planar second base portion 44, and generally parallel to both planar first base portion 28 and planar second base portion 44. Loading pads 86 may include protrusions of first base portion 28. The protrusions may be formed of raised portions of the surfaces surrounding first base portion 28. The protrusions may be generally plateau-shaped in that the raised portions of the first base portion 28 surfaces may extend out to a generally flat outer surface. The outer surfaces of loading pads 86 may constitute raised portions of inward surface 32, outward surface 34, sides 36, 38, and second end 42 depending on the surface they correspond to or are substantially parallel with. For example, the outer surfaces of loading pads 86 that are generally parallel to inward surface 32 may constitute a portion of inward surface 32 and may be referred to herein as inward surface 32. Loading pads 86 may be positioned at corners of first base portion 28 and may be configured to substantially surround at least a portion of the corners of first base portion 28. Loading pads 86 may be raised from their corresponding surfaces a distance of, for example, between about 0.5 millimeter to about 4 millimeters. Loading pads 86 raised from inward surface 32 and constituting a portion of inward surface 32 may be configured to contact first surface 18. Loading pads 86 raised from outward surface 34, sides 36, 38, and second end 42 may be configured to contact wear member 16 when wear member 16 is coupled to mounting base 22 (e.g., in the mounted position).

Second base portion 44 may extend from second end 42 of first base portion 28. Second base portion 44 may have an inward surface 48 configured to be attached to tool 12. Second base portion 44 may also have an outward surface 50 opposite inward surface 48. In addition, second base portion 44 may also have a pair of opposite sides 52, 54 that extend from first base portion 28. Second base portion 44 may also have a pair of opposite ends, lower end 56 and upper end 58, that extend in a direction generally perpendicular to longitudinal direction 30.

Second base portion 44 may also have a protrusion 59 that extends from upper end 58 in a direction generally parallel to first base portion 28. First base portion 28, second base portion 44, and protrusion 59 may form a generally L-shaped mounting base, as depicted in FIGS. 4-5. As shown, the edges and corners of mounting base 22 may be radiused or rounded to reduce stress.

In some embodiments, mounting base 22 may be welded to tool 12. To facilitate such welding, a weld opening may be formed in base 22 to receive weld material, and respective first end 40 and upper end 58 of base portions 28, 44 may include chamfered surfaces to receive weld material. For example, a weld opening in base 22 may be generally oval-shaped, and may be formed in first base portion 28.

Alternatively, a weld opening may be otherwise-shaped, or may be formed in second base portion 44. In yet another alternative, weld openings may be formed in both first and second base portions 28, 44.

At first end 40, first base portion 28 may have a first chamfer surface 82 configured to receive weld material for attaching first base portion 28 to first surface 18 of tool 12. First chamfer surface 82 may extend from an end of inward surface 32 away from tool 12 when inward surface 32 is attached to tool 12. First chamfer surface 82 may extend along first end 40 less than the full length of first end 40.

At upper end 58, second base portion 44 may have a second chamfer surface 84 configured to receive weld material for attaching second base portion 44 to second surface 20 of tool 12. Second chamfer surface 84 may extend from an end of inward surface 48 away from tool 12 when inward surface 48 is attached to tool 12. As shown, second chamfer surface 84 may be positioned at an end of protrusion 59. Second chamfer surface 84 may extend along upper end 58 less than the full length of upper end 58. The weld opening in base 22, first chamfer surface 82, and second chamfer surface 84 in combination may enable welding of mounting base 22 to tool 12 at three locations.

Referring to FIGS. 4-5, sides 52, 54 of second base portion 44 may be configured to be set in from sides 36, 38 of first base portion 28. Sides 52, 54 may also be configured to converge toward each other as they extend away from first base portion 28. As shown, sides 52, 54 may be symmetrical about vertical direction 46. For example, both sides 52, 54 may extend at an angle of about 3 degrees relative to vertical direction 46. In other words, second base portion 44 along latitudinal direction 57 at upper end 58 may be narrower than second base portion 44 at lower end 56. The transition of inward surface 32 to sides 52, 54 at second end 42 and lower end 56 may be radiused to reduce stress as depicted in FIGS. 4-5.

According to one embodiment, as shown in FIGS. 4-5, inward surface 32 of first base portion 28 including the outer surfaces of loading pads 86 that constitute a portion of inward surface 32, may be concave having a radius of curvature. The radius of curvature of inward surface 32 including the outer surfaces of loading pads 86 that constitute a portion of inward surface 32 may generally correspond with the radius of curvature of first surface 18 at heels 15, 17 of tool 12. The corresponding radius of curvatures of the two surfaces may facilitate a flush mating of the outer surfaces of loading pads 86 that constitute a portion of inward surface 32 and first surface 18. Concave inward surface 32 may have a radius of curvature of between about 400 millimeters and about 800 millimeters. In some embodiments the radius of curvature may be between about 500 millimeters and about 700 millimeters. For example, the radius of curvature may be about 600 millimeters. Other radii of curvatures may be utilized. In another alternative embodiment, inward surface 32 of first base portion 28 may be substantially flat. Mounting base 22 having a flat inward surface 32 may be used at first surface 18 of tool 12 where first surface 18 is correspondingly flat to facilitate a flush mating of the surfaces. Besides the difference in the radius of curvature of inward surface 32, mounting base 22 may otherwise be identical in both alternative configurations.

Mounting base 22 may vary in size, thus enabling mounting base 22 to fit a variety of different sizes of tool 12. Although the size of mounting base 22 may vary, the ratio of various dimensions may remain generally the same regardless of the variation in the overall size of mounting base 22 and correspondingly wear member system 14.

Figure 6:
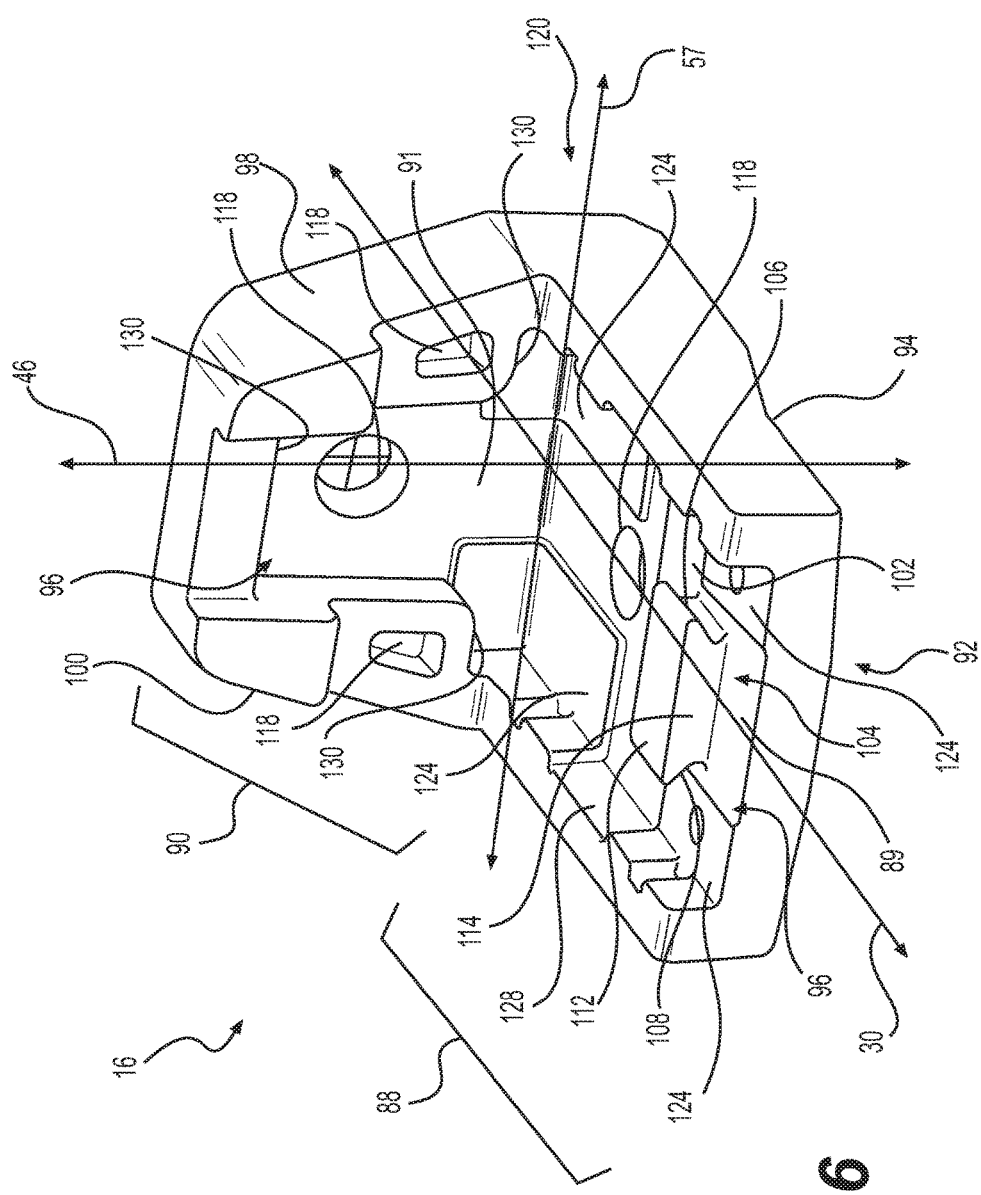
FIG. 6 is a perspective view of an exemplary disclosed wear member of the wear member system of FIG. 3.

FIG. 6 illustrates an exemplary wear member 16 with a plurality of wear indicators 118. As shown, wear member 16 may include a generally planar first wear member portion 88 that extends in longitudinal direction 30. Wear member 16 may also include a generally planar second wear member portion 90, which may extend from first wear member portion 88 in a direction generally perpendicular to first wear member portion 88.

First wear member portion 88 may be generally rectangular, and may have a first inward surface 89. First wear member portion 88 may also have a wear surface 94 opposite first inward surface 89. As shown, a thickness of first wear member portion 88, in a direction parallel to the direction in which second wear member portion 90 extends, may decrease as first wear member portion 88 extends from second wear member portion 90. First wear member portion 88 may define a second opening 102, which may be configured for pass-through of retainer 24 (referring to FIG. 3). Second opening 102 may extend along vertical direction 46 from wear surface 94, through first wear member portion 88, to first inward surface 89. In addition, second opening 102 may be generally rectangle-shaped.

As shown in FIG. 6, wear surface 94 may be convex and have a radius of curvature. The radius of curvature of wear surface 94 may generally correspond with the radius of curvature of first surface 18 at heels 15, 17 of tool 12. The convex wear surface 94 may have a radius of curvature between about 500 millimeters and about 800 millimeters. In some embodiments, the radius of curvature may be between about 600 millimeters and about 700 millimeters. In some other embodiments, the radius of curvature may be between about 650 millimeters and about 660 millimeters. For example, the radius of curvature may be about 655 millimeters.

Second wear member portion 90 may be generally rectangular, and may have a second inward surface 91 contiguous with first inward surface 89 of first wear member portion 88. First inward surface 89 and second inward surface 91 of wear member 16 may define a receiving pocket 96 configured to receive mounting base 22. Receiving pocket 96 may be a generally rectangle-shaped recessed cavity within first wear member portion 88 and second wear member portion 90. As shown, a width of receiving pocket 96 may be less than a width of wear member 16. First wear member portion 88 may include a portion of receiving pocket 96 configured to receive first base portion 28, and second wear member portion 90 may include a portion of receiving pocket 96 configured to receive second base portion 44. The portion of receiving pocket 96 defined by first wear member portion 88 may be open at first end 92, opposite second wear member portion 90. In other words, looking along a longitudinal direction, receiving pocket 96 may be open at first end 92 of first wear member portion 88.

First inward surface 89 of first wear member portion 88 may define a projection 104 adjacent to second opening 102 configured for removably coupling wear member 16 to mounting base 22 when attached to tool 12. Projection 104 may be positioned between second opening 102 and first end 92 of wear member 16. Projection 104 may have opposite engagement side surfaces 106, 108 that may diverge from each other as they extend away from first inward surface 89 within receiving pocket 96 to an upper surface 112 of projection 104. As shown in FIG. 6, engagement side surfaces 106, 108 may be symmetrical about vertical direction 46. For example, engagement side surfaces 106,108 may extend away from first inward surface 89 at angles relative to vertical direction 46, for example of about 45 degrees. Projection 104, when viewed along an axis of first wear member portion 88 generally perpendicular to second wear member portion 90, may be generally isosceles trapezoid-shaped. As shown, the joint between each engagement surface 106, 108 and first inward surface 89 may be rounded to reduce stress within projection 104 and first wear member portion 88. The other joints, edges, and corners of wear member 16 may also be radiused or rounded to reduce stress.

Projection 104 may also have a front surface 114 and a back surface opposite front surface 114 extending from first inward surface 89 to upper surface 112. Front surface 114 and a back surface opposite front surface 114 may be generally perpendicular to first inward surface 89. Projection 104 may be configured to form a dovetail-like joint with a portion of first opening 60 in first base portion 28 of mounting base 22. In addition, projection 104 may be configured such that a height of projection 104 may be less than a depth of receiving pocket 96 so that projection 104 may be positioned completely within receiving pocket 96. In other words, projection 104 may be configured such that no part of projection 104 extends beyond the boundaries of receiving pocket 96.

Referring to FIG. 6, second wear member portion 90 may have opposite side surfaces 98, 100 that extend from first wear member portion 88. Side surfaces 98, 100 initially diverge away from one another along a portion of their lengths and then converge towards one another as they extend from first wear member portion 88. The converging portions of side surfaces 98, 100 may extend at angles relative to vertical direction 46. The angles of side surfaces 98, 100 relative to vertical direction 46 may be between about 15 degrees and about 18 degrees, or in alternative embodiments, substantially parallel.

Wear member 16 may also define one or more wear indicators 118 located in one or more wear surfaces of wear member 16. Wear indicators 118 may be configured to provide an indication as to when wear member 16 should be replaced with a new wear member 16. The indication as to when wear member 16 should be replaced may be, for example when a sufficient portion of the material of wear member 16 is worn off thereby revealing mounting base 22 through one or more of wear indicators 118. In other words, when mounting base 22 becomes visible through wear member 16 at the location of one wear indicator 118, this may act as the indication that wear member 16 should be replaced.

First wear member portion 88 may define a wear indicator 118 formed on inward surface 89 within receiving pocket 96 between second opening 102 and a second end 120. Wear indicator 118 may comprise a recess that is recessed into first wear member portion 88 from first inward surface 89 away from receiving pocket 96. Second wear member portion 90 may also define a wear indicator 118 formed on second inward surface 91 in a central region of second wear member portion 90. Wear indicator 118 formed on second inward surface 91 may comprise a recess that is recessed into second inward surface 91 away from receiving pocket 96. By recessing wear indicators 118 away from receiving pocket 96, the indication that wear member 16 should be replaced may occur prior to any wearing of mounting base 22 occurring. The recessed depth of wear indicators 118 from first inward surface 89 within receiving pocket 96 may be between about 1 millimeter and about 5 millimeters. In other embodiments, the depth may be between about 2 millimeters and about 4 millimeters. For example, the depth may be about 3 millimeters.

Figure 7:
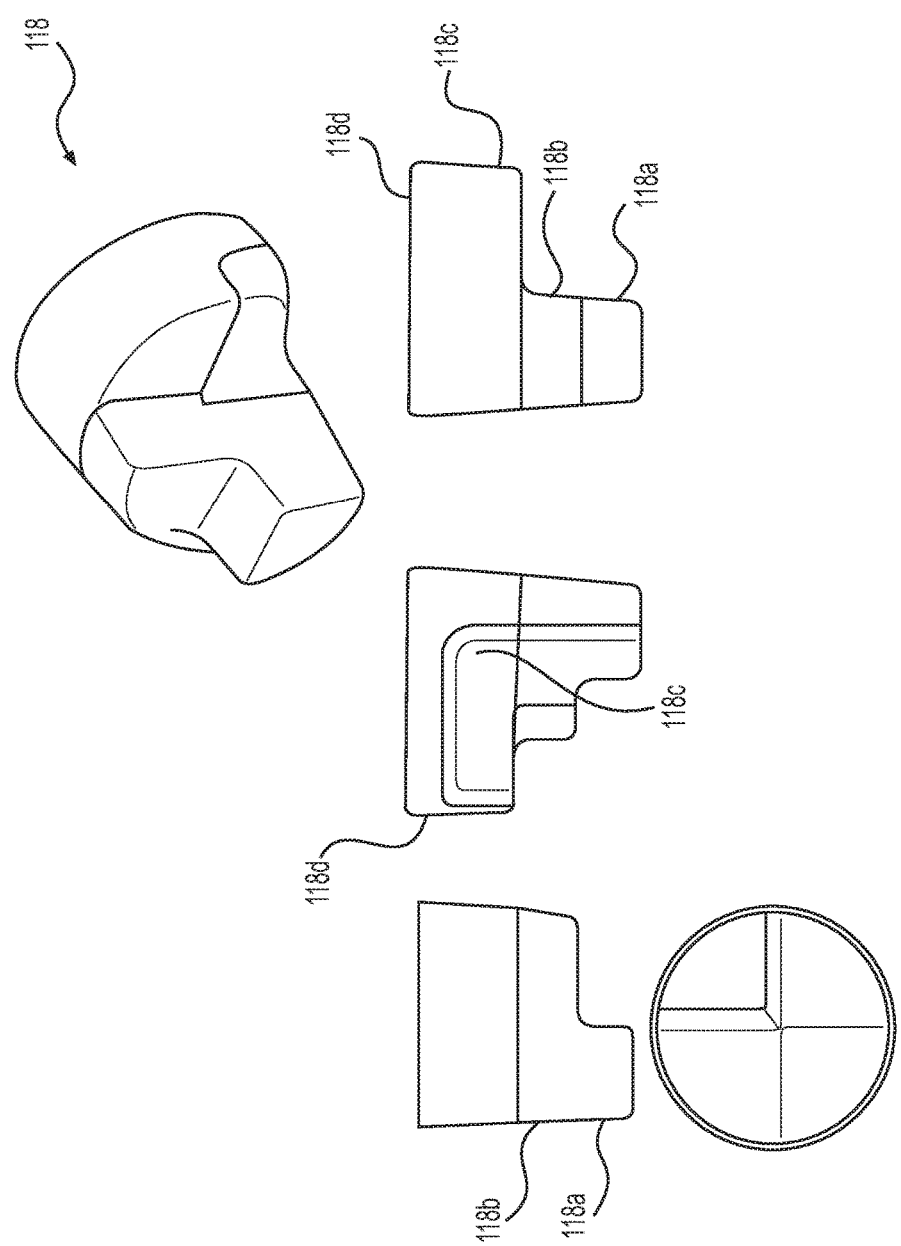
FIG. 7 illustrates several different isometric views of an exemplary wear indicator according to an embodiment of this disclosure.
Figure 8:
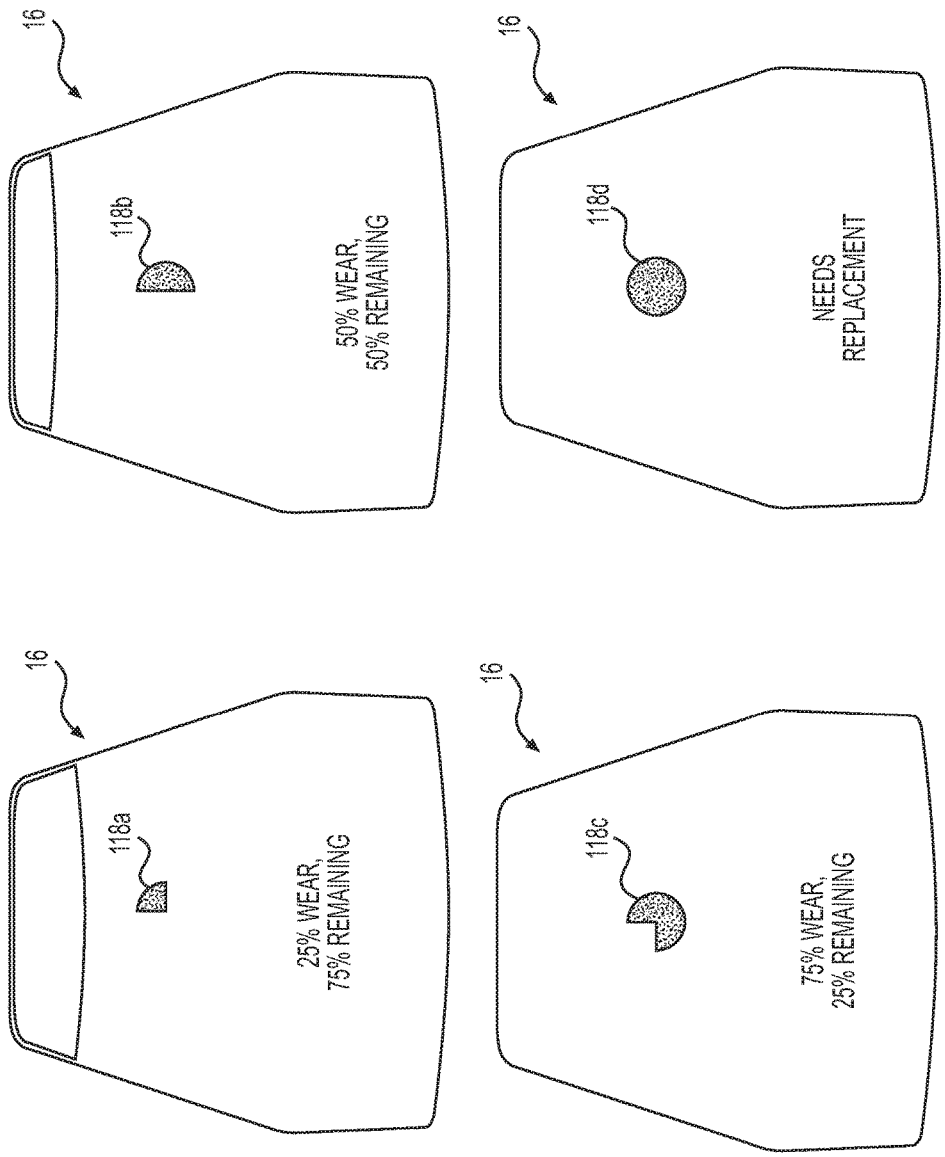
FIG. 8 provides several schematic illustrations of an exemplary wear indicator on a wear member at different stages of wear.

As shown in FIGS. 7 and 8, a wear indicator 118 in accordance with various embodiments of this disclosure may be a plug member configured to be positioned in a region of wear member 16 that is subject to wear. The plug member may be oriented with a central axis of the plug member extending in a direction substantially parallel to a direction of wear of the wear member. "Substantially parallel", as used herein, refers to a direction that is within plus or minus 10 degrees from the direction of the central axis of the plug member. Wear indicator 118 may include a plurality of perceptibly different and distinct axial cross sections taken perpendicular to the central axis of the plug member in axially spaced planes along the central axis. "Perceptibly different and distinct axial cross sections", as used herein, refers to an amount of difference between one or more characteristics of the plug member at each of separate axial cross sections taken at axially spaced positions along and perpendicular to the central axis of the plug member. A first axial cross section that is perceptibly distinct from a second axial cross section has one or more characteristics that can be perceived and distinguished from one or more characteristics of the second axial cross section. A first axial cross section is also a different axial cross section from a second axial cross section when the first and second axial cross sections are axially spaced from each other. Therefore, as used herein, a first axial cross section that is perceptibly different and distinct from a second axial cross section is not only axially spaced from the second axial cross section, but is also distinguishable from the second axial cross section, either by a human observer, or by one or more sensory devices positioned within a range of detection of the plug member. The distinct axial cross sections taken at axially spaced positions along the central axis of the plug member may correspond to successive, incremental amounts of wear on wear member 16. In various embodiments of wear indicator 118 the incremental amount of wear to wear member 16 required to also wear the plug member down to a perceptibly distinct axial cross section may be a certain desired percentage of a total amount of wear that wear member 16 can sustain before it must be replaced or repaired. For example, the plug member may be provided with N perceptibly distinct axial cross sections spaced evenly along the central axis of the plug member in the direction of wear. In this implementation, wear of wear member 16 and wear indicator 118 from one axial cross section of the plug member to a successive, perceptibly distinct axial cross section of the plug member may be indicative of an amount of wear that is 1/Nth of the total wear life for the wear member.

As best seen in FIG. 7, one exemplary embodiment of wear indicator 118 may be a plug that is asymmetrical in at least one direction. In the case of an asymmetrical plug member, a first one of the plurality of perceptibly different and distinct axial cross sections taken in a first plane perpendicular to the central axis may have a discernably different shape than a second one of the axial cross sections taken in a second plane perpendicular to the central axis and spaced from the first plane by a distance corresponding to an incremental amount of wear on the wear member. In the exemplary embodiment illustrated in FIG. 7, wear indicator 118 has four perceptibly different and distinct axial cross sections in the portions 118a, 118b, 118c, and 118d. The appearance of each of the different axial cross sections as viewed in a direction substantially parallel to a direction of wear of wear indicator 118 and wear member 16 is shown in FIG. 8.

Although FIGS. 7 and 8 illustrate an exemplary embodiment of wear indicator 118 having four perceptibly different and distinct axial cross sections, in various alternative embodiments wear indicator 118 may include two or more visually distinct axial cross sections taken perpendicular to the central axis of the asymmetrical plug member. One of the two or more axial cross sections at a first location corresponding to a smaller amount of wear on wear indicator 118 and on wear member 16 than at a second location is a smaller sector of a circle than the axial cross section at the second location. This feature is best seen in the axial end views of wear indicator 118 in position on second wear member portion 90 of wear member 16, as illustrated in FIG. 8.

Figure 9:
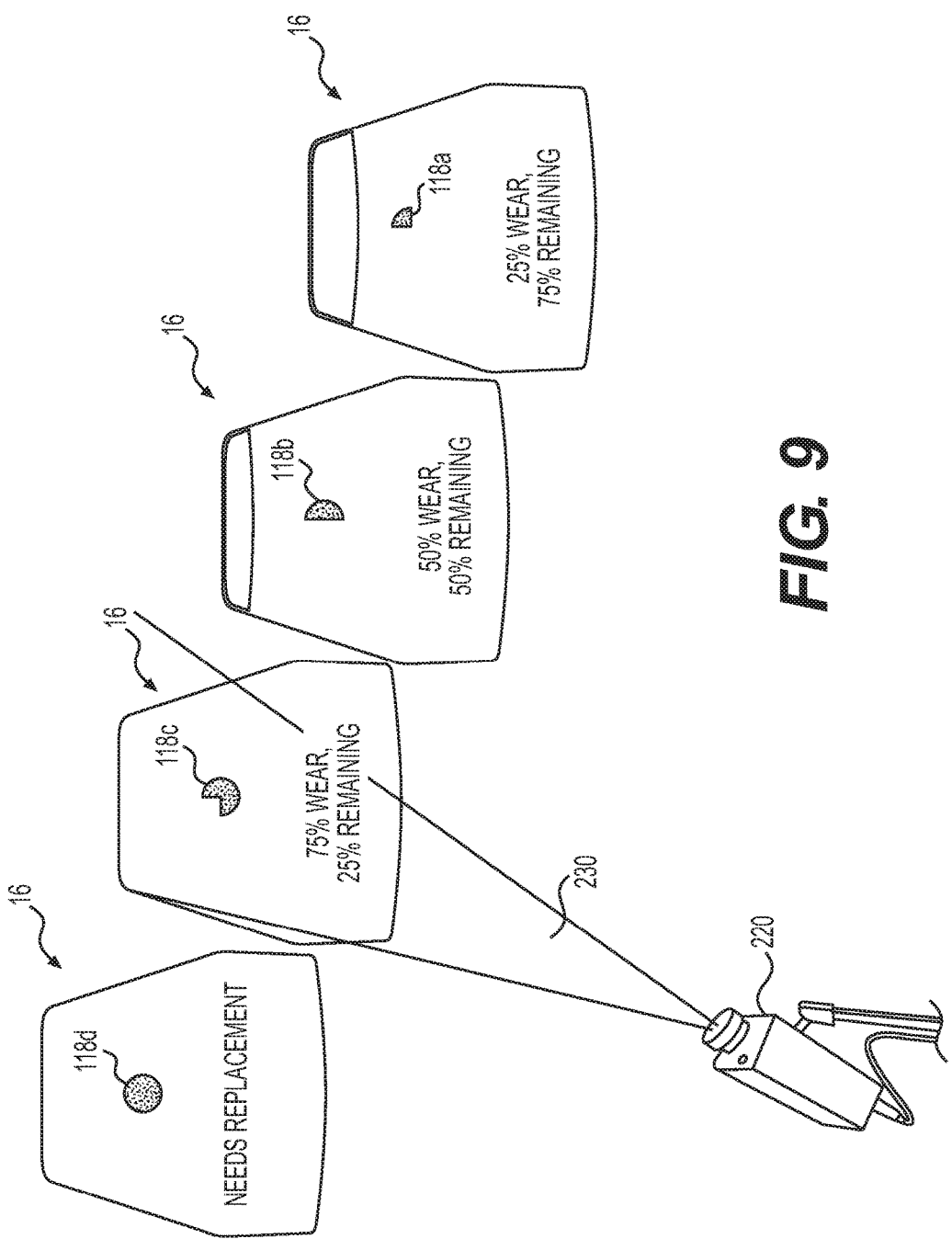
FIG. 9 is a schematic illustration of a wear indicator detection system.

Wear indicator 118 in the exemplary embodiment illustrated in FIGS. 7-9 includes four visually distinct axial cross sections taken perpendicular to the central axis of the asymmetrical plug member. A first one of the axial cross sections corresponds to an approximately 25% worn level for wear member 16. When viewed from one end of wear indicator 118 in a direction substantially parallel to a central axis of the plug member, the first axial cross section appears when wear member 16 and wear indicator 118 are worn down to a first portion 118a of wear indicator 118 having the shape of one quadrant of a circle. A second one of the axial cross sections of wear indicator 118 corresponds to an approximately 50% worn level for wear member 16. When viewed from the one end of wear indicator 118 in a direction substantially parallel to the central axis of the plug member, the second axial cross section appears as a second portion 118b of wear indicator 118 having the shape of one half of a circle. A third one of the axial cross sections corresponds to an approximately 75% worn level for wear member 16. When viewed from the one end of wear indicator 118 in a direction substantially parallel to the central axis of the plug member, the third axial cross section appears as a third portion 118c of wear indicator 118 having the shape of three quadrants of a circle. A fourth one of the axial cross sections corresponds to an approximately 100% worn level for wear member 16. When viewed from the one end of wear indicator 118 in a direction substantially parallel to the central axis of the plug member, the fourth axial cross section appears as a fourth portion 118d of wear indicator 118 having the shape of a full circle. Therefore, as best illustrated in FIGS. 8 and 9, wear indicator 118 positioned, e.g., in second wear member portion 90 of wear member 16, provides perceptibly different and distinct shapes as wear member 16 and wear indicator 118 are incrementally worn down to different axially spaced planes.

In an alternative embodiment of wear indicator 118, at least a first one of the perceptibly different and distinct axial cross sections of the plug member taken in a first plane perpendicular to the central axis may have a discernably different color than a second one of the axial cross sections taken in a second plane perpendicular to the central axis and spaced from the first plane by a distance corresponding to an incremental amount of wear on the wear member. The distinct coloring provided at each of different axial cross sections may be provided in addition to different shapes for each axial cross section in an asymmetrical plug member, or may be provided for the same shape axial cross sections at axially spaced planes along the central axis of a symmetrical plug member.

In another alternative embodiment of wear indicator 118, at least a first one of the perceptibly different and distinct axial cross sections of the plug member taken in a first plane perpendicular to the central axis may include a discernably different material than a second one of the axial cross sections taken in a second plane perpendicular to the central axis and spaced from the first plane by a distance corresponding to an incremental amount of wear on the wear member. In yet another alternative embodiment of wear indicator 118, at least a first one of the perceptibly different and distinct axial cross sections taken in a first plane perpendicular to the central axis may include a discernably different texture than a second one of the axial cross sections taken in a second plane perpendicular to the central axis and spaced from the first plane by a distance corresponding to an incremental amount of wear on the wear member.

In still further alternative embodiments of wear indicator 118, the plug member may be made from at least one of an elastomeric material and a metallic material. The plurality of perceptibly different and distinct axial cross sections of the wear indicator may be discernable from each other as a result of at least one of different shapes, different colors, different materials, different textures, different reactivity to electromagnetic radiation, different reflectivity of electromagnetic radiation, and different absorptivity of electromagnetic radiation.

An automated wear indicator detection system may include one or more sensory devices such as cameras positioned within a range of detection of the one or more wear indicators provided on wear surfaces of wear member 16. FIG. 9 illustrates an exemplary wear indicator detection system, and will be discussed in more detail in the following section.

INDUSTRIAL APPLICABILITY

The disclosed wear indicators may be incorporated into various surfaces subject to wear on wear members of machines. Wear members may include tools such as the bucket 12 shown in FIGS. 1 and 2, or any other tool or component that is subject to wear during use of the machine. The wear indicator according to various implementations of this disclosure may be produced as a separate component and installed into a recess in a surface of a wear member, pressed into a through hole bored through a wear member, or machined or formed directly into the surface of the wear member. In addition, multiple surface wear indicators may be provided on different regions of different surfaces of a wear member of the machine, thereby enabling accurate monitoring of an overall life expectancy for the wear member and facilitating planning of required maintenance intervals.

A wear indicator according to various exemplary embodiments of this disclosure may facilitate the use of a wear indicator detection system for automatically detecting an amount of wear on a surface of a wear member of a machine. As shown in FIG. 9, the wear indicator detection system may include one or more sensory devices 220 positioned within a range of detection 230 of at least one wear indicator 118 located in a surface region of the wear member 16 of the machine. Each of the one or more sensory devices 220 may be configured to discern perceptibly different and distinct axial cross sections of the at least one wear indicator 118 as the surface region of the wear member 16 is worn away by different amounts to successively expose a plurality of distinct axial cross sections of the wear indicator 118.

Although FIG. 9 illustrates a camera being used as the sensory device 220, one of ordinary skill in the art will recognize that automatic detection of perceptibly different and distinct axial cross sections of wear indicator 118 may include the use of one or more sensory devices, wherein each of the one or more sensory devices may include at least one sensor configured to detect electromagnetic radiation, and wherein the electromagnetic radiation may include one or more of visible light, ultraviolet light, infrared light, radio waves, ultrasonic waves and X-rays.

The wear indicator detection system may also include one or more sensory devices configured to transmit signals indicative of the perceptibly different and distinct regions of the at least one wear indicator over one or more of wired, wireless, and cellular communication systems.

The disclosed wear indicator 118 may be manufactured using conventional techniques such as, for example, casting or molding. Alternatively, the disclosed wear indicator may be manufactured using conventional techniques generally referred to as additive manufacturing or additive fabrication. Known additive manufacturing/fabrication processes include techniques such as, for example, 3D printing. 3D printing is a process wherein material may be deposited in successive layers under the control of a computer. The computer controls additive fabrication equipment to deposit the successive layers according to a three-dimensional model (e.g. a digital file such as an AMF or STL file) that is configured to be converted into a plurality of slices, for example substantially two-dimensional slices, that each define a cross-sectional layer of the wear indicator in order to manufacture, or fabricate, the wear indicator. In one case, the disclosed wear indicator would be an original component and the 3D printing process would be utilized to manufacture the wear indicator. In other cases, the 3D process could be used to replicate an existing wear indicator and the replicated wear indicator could be sold as aftermarket parts. These replicated aftermarket wear indicators could be either exact copies of the original wear indicator or pseudo copies differing in only non-critical aspects.

Figure 10:
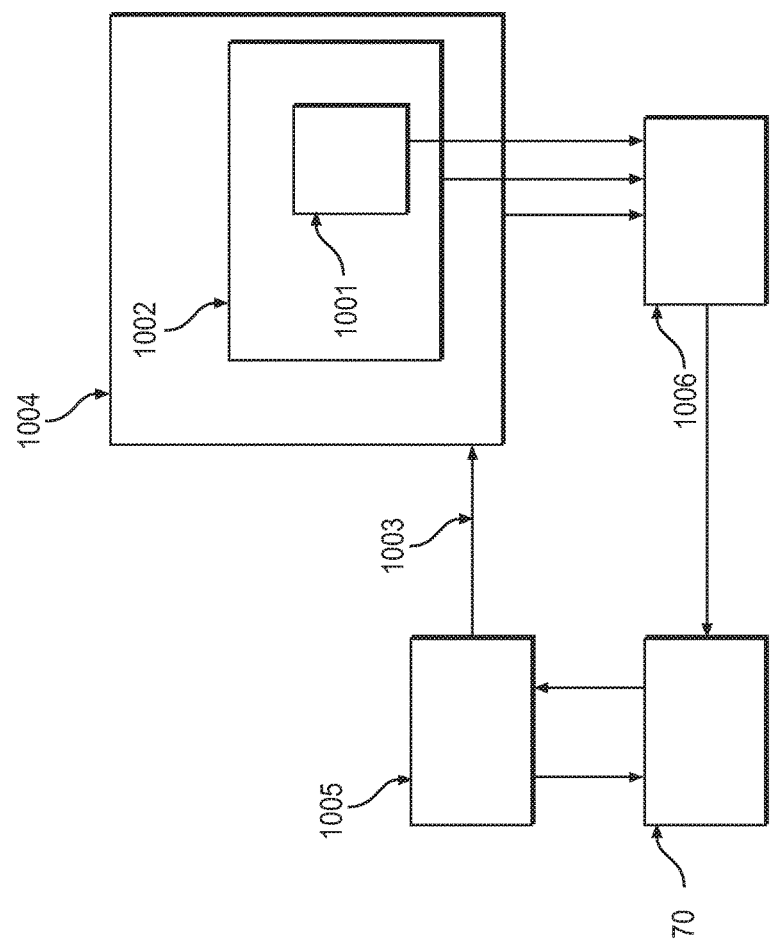
FIG. 10 is a schematic diagram illustrating a process for manufacturing a wear indicator in accordance with various disclosed embodiments.

With reference to FIG. 10, the three-dimensional model 1001 used to represent an original wear indicator 118 may be on a computer-readable storage medium 1002 such as, for example, magnetic storage including floppy disk, hard disk, or magnetic tape; semiconductor storage such as solid state disk (SSD) or flash memory; optical disc storage; magneto-optical disc storage; or any other type of physical memory on which information or data readable by at least one processor may be stored. This storage medium may be used in connection with commercially available 3D printers 1006 to manufacture, or fabricate, the wear indicator 118. Alternatively, the three-dimensional model may be transmitted electronically to the 3D printer 1006 in a streaming fashion without being permanently stored at the location of the 3D printer 1006. In either case, the three-dimensional model constitutes a digital representation of the wear indicator suitable for use in manufacturing the wear indicator.

The three-dimensional model may be formed in a number of known ways. In general, the three-dimensional model is created by inputting data 1003 representing the wear indicator to a computer or a processor 1004 such as a cloud-based software operating system. The data may then be used as a three-dimensional model representing the physical wear indicator. The three-dimensional model is intended to be suitable for the purposes of manufacturing the wear indicator. In an exemplary embodiment, the three-dimensional model is suitable for the purpose of manufacturing the wear indicator by an additive manufacturing technique.

In one embodiment depicted in FIG. 10, the inputting of data may be achieved with a 3D scanner 1005. The method may involve contacting the wear indicator via a contacting and data receiving device and receiving data from the contacting in order to generate the three-dimensional model. For example, 3D scanner 1005 may be a contact-type scanner. The scanned data may be imported into a 3D modeling software program to prepare a digital data set. In one embodiment, the contacting may occur via direct physical contact using a coordinate measuring machine that measures the physical structure of the wear indicator by contacting a probe with the surfaces of the wear indicator in order to generate a three-dimensional model. In other embodiments, the 3D scanner 1005 may be a non-contact type scanner and the method may include directing projected energy (e.g. light or ultrasonic) onto the wear indicator to be replicated and receiving the reflected energy. From this reflected energy, a computer would generate a computer-readable three-dimensional model for use in manufacturing the wear indicator. In various embodiments, multiple 2D images can be used to create a three-dimensional model. For example, 2D slices of a 3D object can be combined to create the three-dimensional model. In lieu of a 3D scanner, the inputting of data may be done using computer-aided design (CAD) software. In this case, the three-dimensional model may be formed by generating a virtual 3D model of the disclosed wear indicator using the CAD software. A three-dimensional model would be generated from the CAD virtual 3D model in order to manufacture the wear indicator.

The additive manufacturing process utilized to create the disclosed wear indicator may involve materials such as plastic, rubber, metal, etc. In some embodiments, additional processes may be performed to create a finished product. Such additional processes may include, for example, one or more of cleaning, hardening, heat treatment, material removal, and polishing. Other processes necessary to complete a finished product may be performed in addition to or in lieu of these identified processes.

It will be apparent to those skilled in the art that various modifications and variations can be made to the disclosed wear indicator, wear member, and/or wear indicator detection system. Other embodiments will be apparent to those skilled in the art from consideration of the specification and practice of the disclosed method and apparatus. It is intended that the specification and examples be considered as exemplary only, with a true scope being indicated by the following claims and their equivalents.

What is claimed is:

1. A wear indicator for a wear member of a machine wherein the wear member is removably coupled to a mounting base fixed to a portion of the machine, wherein the portion of the machine is subject to wear during use of the machine, the wear member contacting the mounting base along an inward-facing surface of the wear member, the wear indicator comprising:
   a plug member configured to be positioned in a recess formed into the inward-facing surface of the wear member in a region of the wear member subject to wear, the plug member being oriented with a central axis extending in a direction substantially parallel to a direction of wear of the wear member; and
   the wear indicator including a plurality of perceptibly different and distinct axial cross sections taken perpendicular to the central axis of the plug member in axially spaced planes along the central axis.

2. The wear indicator of claim 1, wherein the plug member is asymmetrical in at least one direction, and a first one of the plurality of perceptibly different and distinct axial cross sections taken in a first plane perpendicular to the central axis has a discernably different shape than a second one of the axial cross sections taken in a second plane perpendicular to the central axis and spaced from the first plane by a distance corresponding to an incremental amount of wear on the wear member.

3. The wear indicator of claim 2, wherein the wear indicator includes at least two visually distinct axial cross sections taken perpendicular to the central axis of the asymmetrical plug member, and wherein one of the at least two axial cross sections at a first location corresponding to a smaller amount of wear on the plug member and the wear member than at a second location is a smaller sector of a circle than the axial cross section at the second location.

4. The wear indicator of claim 3, wherein the wear indicator includes four visually distinct axial cross sections taken perpendicular to the central axis of the asymmetrical plug member, and wherein a first one of the axial cross sections corresponding to an approximately 25% worn level for the wear member is one quadrant of a circle, a second one of the axial cross sections corresponding to an approximately 50% worn level for the wear member is one half of a circle, a third one of the axial cross sections corresponding to an approximately 75% worn level for the wear member is three quadrants of a circle, and a fourth one of the axial cross sections corresponding to an approximately 100% worn level for the wear member is a full circle.

5. The wear indicator of claim 1, wherein a first one of the perceptibly different and distinct axial cross sections taken in a first plane perpendicular to the central axis has a discernably different color than a second one of the axial cross sections taken in a second plane perpendicular to the central axis and spaced from the first plane by a distance corresponding to an incremental amount of wear on the wear member.

6. The wear indicator of claim 1, wherein a first one of the perceptibly different and distinct axial cross sections taken in a first plane perpendicular to the central axis comprises a discernably different material than a second one of the axial cross sections taken in a second plane perpendicular to the central axis and spaced from the first plane by a distance corresponding to an incremental amount of wear on the wear member.

7. The wear indicator of claim 1, wherein a first one of the perceptibly different and distinct axial cross sections taken in a first plane perpendicular to the central axis comprises a discernably different texture than a second one of the axial cross sections taken in a second plane perpendicular to the central axis and spaced from the first plane by a distance corresponding to an incremental amount of wear on the wear member.

8. The wear indicator of claim 1, wherein the plug member is made from an elastomeric material, and the plurality of perceptibly different and distinct axial cross sections are discernable from each other as a result of at least one of different shapes and different colors.

9. The wear indicator of claim 1, wherein the plug member is made at least in part from one or more materials at each of the plurality of axial cross sections having discernably different and distinct perceptible characteristics at each of the plurality of axial cross sections including at least one of different reactivity to electromagnetic radiation, different reflectivity of electromagnetic radiation, and different absorptivity of electromagnetic radiation.

10. A method of creating a computer-readable three-dimensional model suitable for use in manufacturing the wear indicator of claim 1, the method comprising:
inputting data representing the wear indicator to a computer; and
using the data to represent the wear indicator as a three-dimensional model, the three dimensional model being suitable for use in manufacturing the wear indicator.

11. The method of claim 10, wherein the inputting of data includes one or more of using a contact-type 3D scanner to contact the wear indicator, using a non-contact 3D scanner to project energy onto the wear indicator and receive reflected energy, and generating a virtual three-dimensional model of the wear indicator using computer-aided design (CAD) software.

12. A computer-readable three-dimensional model suitable for use in manufacturing the wear indicator of claim 1.

13. A computer-readable storage medium having data stored thereon representing a three-dimensional model suitable for use in manufacturing the wear indicator of claim 1.

14. A method for manufacturing the wear indicator of claim 1, the method comprising the steps of:
providing a computer-readable three-dimensional model of the wear indicator, the three-dimensional model being configured to be converted into a plurality of slices that each define a cross-sectional layer of the wear indicator; and
successively forming each layer of the wear indicator by additive manufacturing.

15. A wear member of a machine,
the wear member being removably coupled to a mounting base fixed to a portion of the machine, wherein the portion of the machine is subject to wear during use of the machine;
the wear member contacting the mounting base along at least one inward-facing surface of the wear member, and the wear member comprising:
at least one surface subject to wear during operation of the machine, the at least one surface including at least one wear indicator configured to provide an indication of an amount of wear of a region of the at least one surface of the wear member;
the at least one wear indicator comprising a plug configured to be positioned in a recess formed into the at least one inward-facing surface of the wear member in the region of the at least one surface of the wear member, the plug being oriented with a central axis of the plug extending in a direction substantially parallel to a direction of wear of the machine wear member, and the wear indicator including a plurality of perceptibly different and distinct axial cross sections taken perpendicular to the central axis of the plug in axially spaced planes along the central axis.

16. The wear member according to claim 15, wherein the plug is asymmetrical in at least one direction, and a first one of the plurality of perceptibly different and distinct axial cross sections of the wear indicator taken in a first plane perpendicular to the central axis has a discernably different shape than a second one of the axial cross sections taken in a second plane perpendicular to the central axis and spaced from the first plane by a distance corresponding to an incremental amount of wear on the wear member.

17. The wear member of claim 16, wherein the wear indicator includes at least two visually distinct axial cross sections taken perpendicular to the central axis of the asymmetrical plug, and wherein one of the at least two axial cross sections at a first location corresponding to a smaller amount of wear on the plug and the at least one surface of the wear member than at a second location is a smaller sector of a circle than the axial cross section at the second location.

18. The wear member of claim 17, wherein the wear indicator includes four visually distinct axial cross sections taken perpendicular to the central axis of the asymmetrical plug, and wherein a first one of the axial cross sections corresponding to an approximately 25% worn level for the wear member is one quadrant of a circle, a second one of the axial cross sections corresponding to an approximately 50% worn level for the wear member is one half of a circle, a third one of the axial cross sections corresponding to an approximately 75% worn level for the wear member is three quadrants of a circle, and a fourth one of the axial cross sections corresponding to an approximately 100% worn level for the wear member is a full circle.

19. The wear member of claim 15, wherein a first one of the perceptibly different and distinct axial cross sections of the wear indicator taken in a first plane perpendicular to the central axis of the plug has a discernably different color than a second one of the axial cross sections taken in a second plane perpendicular to the central axis and spaced from the first plane by a distance corresponding to an incremental amount of wear on the wear member.

20. The wear member of claim 15, wherein a first one of the perceptibly different and distinct axial cross sections of the wear indicator taken in a first plane perpendicular to the central axis of the plug comprises a discernably different material than a second one of the axial cross sections taken in a second plane perpendicular to the central axis and spaced from the first plane by a distance corresponding to an incremental amount of wear on the wear member.

21. The wear member of claim 15, wherein a first one of the perceptibly different and distinct axial cross sections of the wear indicator taken in a first plane perpendicular to the central axis of the plug comprises a discernably different texture than a second one of the axial cross sections taken in a second plane perpendicular to the central axis and spaced from the first plane by a distance corresponding to an incremental amount of wear on the wear member.

22. The wear member of claim 15, wherein the plug of the at least one wear indicator is made from at least one of an elastomeric material and a metallic material, and the plurality of perceptibly different and distinct axial cross sections of the wear indicator are discernable from each other as a result of at least one of different shapes, different colors, different materials, different textures, different reactivity to electromagnetic radiation, different reflectivity of electromagnetic radiation, and different absorptivity of electromagnetic radiation.

23. A wear indicator detection system for automatically detecting an amount of wear on a surface of a wear member of a machine, the wear indicator detection system comprising:
one or more sensory devices positioned within a range of detection of at least one wear indicator located in a surface region of the wear member of the machine;
each of the one or more sensory devices being configured to discern perceptibly different and distinct regions of the at least one wear indicator as the surface region of the wear member is worn away by different amounts to expose a plurality of spaced regions of the wear indicator;
the wear member being removably coupled to a mounting base fixed to a portion of the machine, wherein the portion of the machine is subject to wear during use of the machine;
the wear member contacting the mounting base along at least one inward-facing surface of the wear member; and
the at least one wear indicator comprising a plug configured to be positioned in a recess formed into the at least one inward-facing surface of the wear member in the surface region of the wear member, the plug being oriented with a central axis of the plug extending in a direction substantially parallel to a direction of wear of the machine wear member, and the wear indicator including a plurality of perceptibly different and distinct axial cross sections taken perpendicular to the central axis of the plug in axially spaced planes along the central axis.

24. The wear indicator detection system according to claim 23, wherein each of the one or more sensory devices includes at least one of a sensor configured to detect electromagnetic radiation, wherein the electromagnetic radiation includes one or more of visible light, ultraviolet light, infrared light, radio waves, ultrasonic waves and X-rays.

25. The wear indicator detection system according to claim 24, wherein each of the one or more sensory devices is further configured to transmit signals indicative of the perceptibly different and distinct regions of the at least one wear indicator over one or more of wired, wireless, and cellular communication systems.

* * * * *